United States Patent [19]

Karnovsky et al.

[11] Patent Number: 4,668,661
[45] Date of Patent: May 26, 1987

[54] SLEEP INDUCING AGENTS

[75] Inventors: Manfred J. Karnovsky, Cambridge, Mass.; James M. Krueger, Highland Park, Ill.; John R. Pappenheimer, Cambridge, Mass.

[73] Assignee: President & Fellows of Harvard College, Cambridge, Mass.

[21] Appl. No.: 664,064

[22] Filed: Oct. 23, 1984

[51] Int. Cl.$^4$ .................. A61K 37/02; C07K 9/00
[52] U.S. Cl. .................................... 514/8; 530/322
[58] Field of Search .................. 514/18, 8; 530/322

[56] References Cited

U.S. PATENT DOCUMENTS 4,342,748 8/1982 Pappenheimer et al. ............. 424/95
4,391,800 7/1983 Durette et al. ........................ 514/18

OTHER PUBLICATIONS

Ladesic, Biochimica et Biophysica Acta, vol. 678, pp. 12–17 (1981).
Klaic, Carbohydrate Research, vol. 110, pp. 320–325 (1982).
Klaic et al., Carbohydrate Research, vol. 123, pp. 168–172 (1983).
Keglevic et al., Eur. J. Biochem., vol. 42, 389–400 (1974).
Keglevic et al., Biochimica et Biophysica Acta, vol. 585, pp. 273–281 (1979).
Tomasic, Biochimica et Biophysica Acta, vol. 629, pp. 77–82 (1980).

Primary Examiner—Delbert R. Phillips

[57] ABSTRACT

A compound capable of inducing sleep in mammals comprising a peptidoglycan monomer obtained by lysozyme digestion of linear non-crosslinked peptidoglycan polymer chains present in culture fluids of penicillin-treated *Brevibacterium divaricatum* mutant NRRL 2311 together with hydrolysis of at least one amide group of said monomer.

24 Claims, No Drawings

SLEEP INDUCING AGENTS

The invention described herein was made in the course of work with U.S. Government support, and the Government has certain rights in the invention.

This invention relates to agents for inducing sleep in mammals and pertains more specifically to a deamidated peptidoglycan monomer.

Pappenheimer et al. U.S. Pat. No. 4,342,748 describes a sleep-promoting factor having the composition muramic acid, alanine, diaminopimelic acid, and glutamic acid or glutamine. In addition, there has previously been reported the isolation and purification of a peptidoglycan monomer by lysozyme digestion of uncrosslinked peptidoglycan chains isolated from culture fuids of a penicillin-treated mutant of *Brevibacterium divaricatum* NRRL-2311. Keglevic et al., Eur. J. Biochem., Vol. 42, 389–400 (1974). The monomer has been erroneously reported to have the following composition

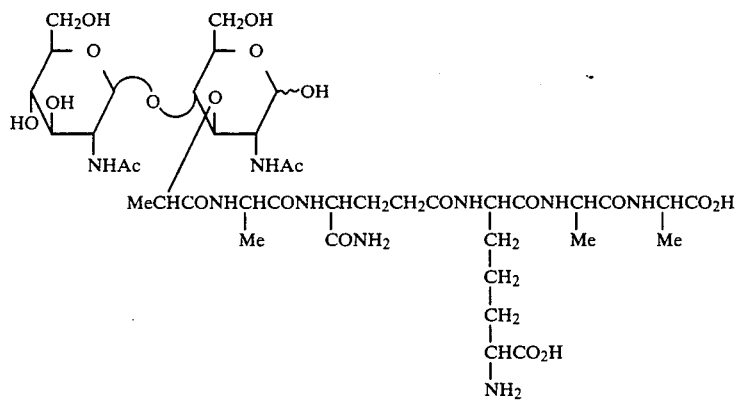

also denominated GlcNAc-MurNAc-L-Ala-D-isoglutamine-mesodiaminopimelic acid-D-Ala-D-Ala, Keglevic et al., Biochimica et Biophysica Acta, Vol. 585, 273-281 (1979); Tomasic, Ibid., Vol. 629, 77–82 (1980); Ladesic, Ibid. Vol. 678, 12–17 (1981); Klaic, Carbohydrate Research, Vol. 110, 320–325, (1982). However, the composition in fact does not contain a diaminopimelic acid moiety but rather a diaminopimelic amide moiety as eluciated by Klaic et al., Carbohydrate Research, Vol. 123, 168-172 (1983), and is stated to have the following composition

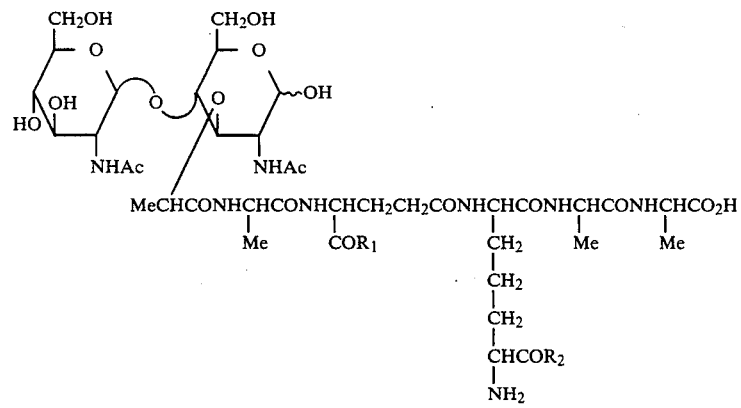

in which $R_1$ and $R_2$ is each $-NH_2$ (I). This isolated and purified peptidoglycan monomer has no sleep-inducing capability when administered to mammals, even when injected intraventricularly. It has also been found that the foregoing peptidoglycan monomer produced by *B. divaricatum* exists at least in part in the anhydromuramyl form in which the muramyl component is internally cyclized at the 1,6-positions by removal of water, viz:

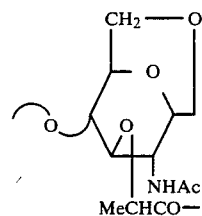

The 1,6-anhydromuramyl analogue in which $R_1$ and $R_2$ is each $NH_2$ (II) is also inactive as a sleep-inducing agent.

It has now been found that the foregoing peptidoglycan monomer, after removal of one or both of the unsubstituted amide groups $R_1$ and $R_2$ by hydrolysis, is an effective sleep-inducing agent in mammals. It is believed that hydrolysis, e.g., by heating in dilute aqueous acid, causes deamidation initially of the diaminopimelic amide moiety to a diaminopimelic acid moiety by converting $R_2$ from $-NH_2$ to $-OH$, and that further hydrolysis causes in addition deamidation of the isoglutamine moiety to a glutamic acid moiety by converting $R_1$ from $-NH_2$ to $-OH$, resulting in a mixture of the two monoamide products having the composition

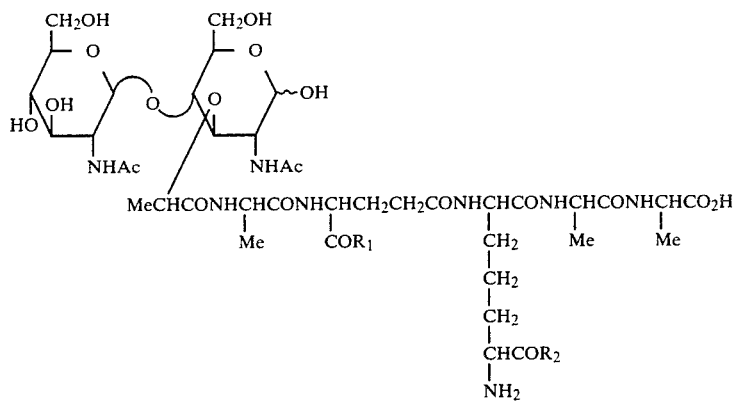

MeCHCONHCHCONHCHCH$_2$CH$_2$CONHCHCONHCHCONHCHCO$_2$H
   |          |                         |       |       |
  Me    COR$_1$               CH$_2$  Me   Me
                                |
                             CH$_2$
                              |
                             CH$_2$
                              |
                             CHCOR$_2$
                             |
                             NH$_2$ in which (1) $R_1$ is —NH$_2$ and $R_2$ is —OH, and (2) in which $R_1$ is —OH and $R_2$ is —NH$_2$, and the triacid product (3) in which $R_1$ and $R_2$ are both OH. The corresponding 1,6-anhydromuramyl products are also effective sleep-inducing agents.

One or more of the compounds of the present invention can be administered to mammals orally, rectally, intravenously, intramuscularly, intraperitoneally or intraventricularly in the form of a composition containing the active agent in combination with any non-toxic physiologically acceptable carrier, many of which are well known in the art. The exact dosage form and size of dose depend upon body size and case history of the individual. In general, an amount of active agent from 2 to 50 ng per kg body weight is sufficient to induce slow wave sleep when injected intraventricularly.

Biological assays for sleep-promoting activity were performed on rabbits provided with chronically implanted ventricular guide tubes and four epidural screw electrodes for EEG. The animals were allowed at least one week to recover from surgery prior to their use for assays. Samples for testing were taken up in sterile, artificial cerebrospinal fluid (155 mM NaCl, 3 mM KCl, 1.15 mM CaCl$_2$, and 0.96 mM MgCl$_2$) and a total of 0.3 ml solution was infused intraventricularly at the rate of 7 μl/min through a No. 26 hypodermic needle inserted through the guide tube. Following the infusion and removal of the infusion probe the animals were left undisturbed for 6–8 hours while EEG and bodily movements were recorded. Slow wave sleep (SWS) was scored in two ways: (i) by conventional subjective scoring of the duration of SWS from polygraph records and (ii) by digital print-out of integrated mean rectified cortical slow waves ($\frac{1}{2}$–4 Hz), thus obtaining a measure of the amplitude as well as duration of delta wave EEG activity. Control animals were also assayed at the same time.

The following example is intended to illustrate more fully the nature of the present invention without acting as a limitation upon its scope.

EXAMPLE

About 1 mg of the peptidoglycan monomer obtained by lysozyme digestion of uncrosslinked peptidoglycan chains isolated from culture fluids of a penicillin-treated mutant of *Brevibacterium divaricatum* NRRL 2311, prepared as described in Klaic, Carbohydr. Res., Vol. 110, 320–325 (1982), was separated into its muramyl-containing and its 1,6-anhydromuramyl-containing forms by conventional chromatographic procedures. A Waters HPLC model 6000A binary pumping system with solvent programmer and a Waters μ Bondpak C$_{18}$ reversed-phase column were employed; for detection there were used a Beckman model 160 absorbance detector operated at 214 nm and a Hewlett Packard 3390A integrator. The solvent program used for separation was linear from 0 to 10% acetonitrile (containing 0.035% trifluoroacetic acid) in water (containing 0.05% trifluoroacetic acid) over a period of 25 minutes at a flow rate of 1.5 ml/min. Each of the two products, in the amount of 1 mg., was stirred into 1.2 ml of 0.1 normal hydrochloric acid and heated at 100° C., for one hour. The reaction mixture was then subjected to vacuum and to freezing to remove the water and hydrochloric acid. Methyl alcohol was added to the residue, and the mix was again subjected to vacuum and freezing. The resulting crude deamidated products contained a mixture of a small amount of residual unchanged monomer, the monomer in which the diaminopimelic amide had been converted to diaminopimelic acid (III), the monomer in which the isoglutamine had been converted to glutamic acid (IV), and the monomer in which both unsubstituted amide moieties had been converted to carboxylic acid moieties (V).

The crude product mixtures were subjected to the high pressure liquid chromatography procedure described above. The fractions containing a mixture of the monoamides (III) and (IV) were freeze-dried to provide a dry solid purified product free from the peptidoglycan monomer starting material and free from the fully hydrolyzed tricarboxylic acid; the two products each consisted essentially of a mixture of pure monoamides (III and IV), in one case the muramyl component being in the form shown in formula (I) above and in the other being in the corresponding 1,6-anhydromuranyl form.

The peptidoglycan monomer, the 1,6-anhydromuramyl variant and the two partially hydrolyzed mixtures containing the monoamides were then assayed as described above for sleep-promoting or -inducting activity in rabbits, with the results shown in the following table:

TABLE

| Substance | Dose (pmoles) | No. Animals | % SWS (hrs 2–6 post-infusion) Control | Experimental |
|---|---|---|---|---|
| Peptidoglycan | 100 | 4 | 41 ± 2 | 38 ± 1 |
| Monomer I | 1000 | 4 | 38 ± 4 | 39 ± 2 |
| Peptidoglycan | 0.3 | 4 | 45 ± 2 | 48 ± 4 |
| Monomer having | 3 | 4 | 44 ± 3 | 45 ± 1 |

TABLE-continued

| Substance | Dose (pmoles) | No. Animals | % SWS (hrs 2-6 post-infusion) Control | % SWS (hrs 2-6 post-infusion) Experimental |
|---|---|---|---|---|
| 1,6-Anhydro-muramyl Group | 30 | 2 | 33, 36 | 53, 67 |
| Mixture of amides from I | 1 | 4 | 44 ± 1 | 47 ± 1 |
|  | 3 | 3 | 42 ± 2 | 54 ± 6 |
|  | 9 | 3 | 43 ± 2 | 51 ± 1 |
| Mixture of amides from monomer having 1,6-anhydro-muramyl group | 0.3 | 5 | 40 ± 2 | 44 ± 3 |
|  | 3 | 10 | 42 ± 2 | 55 ± 2 |
|  | 30 | 2 | 38, 47 | 64, 58 |

It is bellieved that the compounds having the greatest sleep-inducing activity are the monoamides having the structure (III) above in which $R_1$ is —$NH_2$ and $R_2$ is —OH and the corresponding 1,6-anhydromuramyl form of monoamide, but the corresponding monoamide having the structure IV and the triacid having the structure V are also active.

What is claimed is:

1. A compound capable of inducing sleep in mammals having the formula

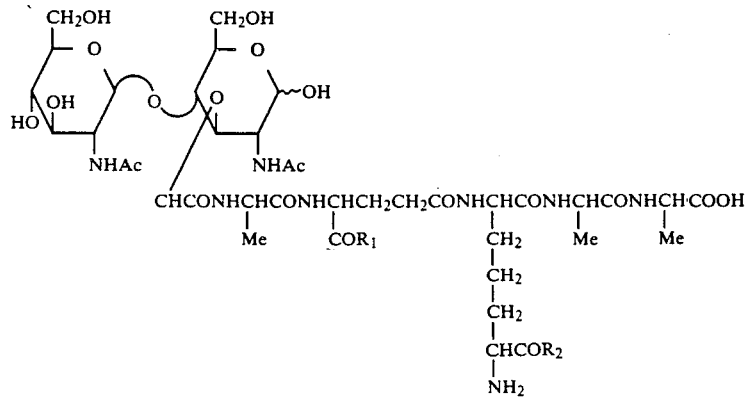

wherein $R_1$ is $NH_2$ or OH and $R_2$ is $NH_2$ or OH, provided that $R_1$ and $R_2$ are not both $NH_2$.

2. The compound of claim 1 wherein $R_1$ is $NH_2$ and $R_2$ is OH.

3. The compound of claim 1 wherein $R_1$ is OH and $R_2$ is $NH_2$.

4. The compound of claim 1 wherein $R_1$ is OH and $R_2$ is OH.

5. A pharmaceutical composition capable of inducing sleep in mammals which comprises a physiologically acceptable carrier and a compound as claimed in claim 1.

6. A pharmaceutical composition capable of inducing sleep in mammals which comprises a physiologically acceptable carrier and a compound as claimed in claim 2.

7. A pharmaceutical composition capable of inducing sleep in mammals which comprises a physiologically acceptable carrier and a compound as claimed in claim 3.

8. A pharmaceutical composition capable of inducing sleep in mammals which comprises a physiologically acceptable carrier and a compound as claimed in claim 4.

9. A method for inducing sleep in a mammal which comprises administering to the mammal an effective sleep inducing amount of the compound of claim 1.

10. A method for inducing sleep in a mammal which comprises administering to the mammal an effective sleep inducing amount of the compound of claim 2.

11. A method for inducing sleep in a mammal which comprises administering to the mammal an effective sleep inducing amount of the compound of claim 3.

12. A method for inducing sleep in a mammal which comprises administering to the mammal an effective sleep inducing amount of the compound of claim 4.

13. A compound capable of inducing sleep in mammals having the formula

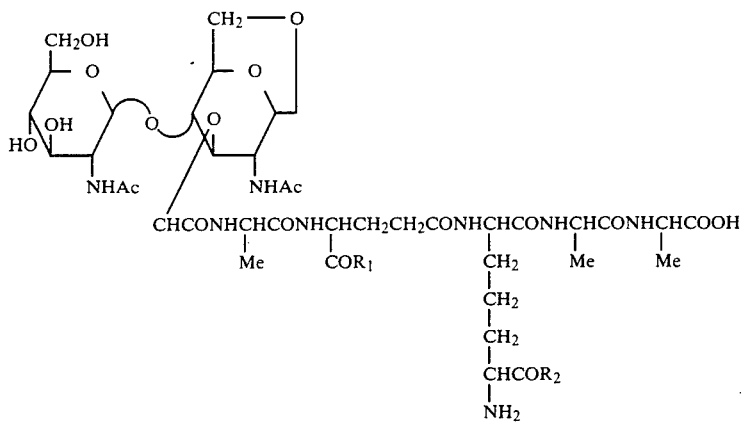

wherein $R_1$ is $NH_2$ or OH and $R_2$ is $NH_2$ or OH, provided that $R_1$ and $R_2$ are not both $NH_2$.

14. The compound of claim 13 wherein $R_1$ is $NH_2$ and $R_2$ is OH.

15. The compound of claim 13 wherein $R_1$ is OH and $R_2$ is $NH_2$.

16. The compound of claim 13 wherein $R_1$ is OH and $R_2$ is OH.

17. A pharmaceutical composition capable of inducing sleep in mammals which comprises a physiologically acceptable carrier and a compound as claimed in claim 13.

18. A pharmaceutical composition capable of inducing sleep in mammals which commprises a physiologically acceptable carrier and a compound as claimed in claim 14.

19. A pharmaceutical composition capable of inducing sleep in mammals which comprises a physiologically acceptable carrier and a compound as claimed in claim 15.

20. A pharmaceutical composition capable of inducing sleep in mammals which comprises a physiologically acceptable carrier and a compound as claimed in claim 16.

21. A method for inducing sleep in a mammal which comprises administering to the mammal an effective sleep inducing amount of the compound of claim 13.

22. A method for inducing sleep in a mammal which comprises administering to the mammal an effective sleep inducing amount of the compound of claim 14.

23. A method for inducing sleep in a mammal which comprises administering to the mammal an effective sleep inducing amount of the compound of claim 15.

24. A method for inducing sleep in a mammal which comprises administering to the mammal an effective sleep inducing amount of the compound of claim 16.

* * * * *

UNITED STATES PATENT AND TRADEMARK OFFICE
CERTIFICATE OF CORRECTION

PATENT NO. : 4,668,661

DATED : May 26, 1987

INVENTOR(S) : Manfred J. Karnovsky et al

It is certified that error appears in the above-identified patent and that said Letters Patent are hereby corrected as shown below:

On the front page of the patent following the information in [56] and before [57], please insert the following:

Insert: --Attorney, Agent, or Firm - Weiser & Stapler--

Signed and Sealed this

Ninth Day of February, 1988

*Attest:*

DONALD J. QUIGG

*Attesting Officer*     *Commissioner of Patents and Trademarks*